(12) United States Patent
Cornwell et al.

(10) Patent No.: US 12,194,017 B2
(45) Date of Patent: Jan. 14, 2025

(54) THERAPEUTIC COMPOSITION DELIVERY DEVICE

(71) Applicant: Helios Cardio Inc., Weston, MA (US)

(72) Inventors: Kevin Cornwell, Holliston, MA (US); Yiannis Monovoukas, Weston, MA (US); Peter Jackson, Brookline, MA (US); Clayton Kaiser, Nashville, TN (US)

(73) Assignee: Helios Cardio Inc., Weston, MA (US)

( * ) Notice: Subject to any disclaimer, the term of this patent is extended or adjusted under 35 U.S.C. 154(b) by 0 days.

(21) Appl. No.: 17/895,004

(22) Filed: Aug. 24, 2022

(65) Prior Publication Data

US 2023/0071220 A1    Mar. 9, 2023

Related U.S. Application Data

(60) Provisional application No. 63/236,836, filed on Aug. 25, 2021.

(51) Int. Cl.
| | | |
|---|---|---|
| *A61K 31/343* | (2006.01) | |
| *A61B 18/00* | (2006.01) | |
| *A61K 9/70* | (2006.01) | |
| *A61K 31/167* | (2006.01) | |
| *A61K 33/06* | (2006.01) | |

(Continued)

(52) U.S. Cl.
CPC .......... *A61K 31/343* (2013.01); *A61K 9/7046* (2013.01); *A61K 31/167* (2013.01); *A61K 33/06* (2013.01); *A61L 27/3633* (2013.01); *A61L 27/54* (2013.01); *A61B 2018/00404* (2013.01)

(58) Field of Classification Search
CPC .. A61K 31/343; A61K 9/7046; A61K 31/167; A61K 33/06; A61L 27/3633; A61L 27/54; A61L 2300/402; A61L 2430/40; A61B 2018/00404
See application file for complete search history.

(56) References Cited

U.S. PATENT DOCUMENTS 7,354,702 B2 *  4/2008  Dai ...................... A61L 27/507
                                                                     435/395
8,980,296 B2   3/2015  Matheny et al.
(Continued)

FOREIGN PATENT DOCUMENTS

| EP | 2 398 502 B1 | 12/2011 |
|---|---|---|
| EP | 3 000 472 B1 | 4/2017 |

OTHER PUBLICATIONS

Habbab et al, "Intrapericardial Amiodarone for the Prevention of Postoperative Atrial Fibrillation", Jour of Cardiac Surgery, vol. 31, issue 4, 2016, pp. 253-258. (Year: 2016).*

(Continued)

*Primary Examiner* — Benjamin J Packard
*Assistant Examiner* — Joshua A Atkinson
(74) *Attorney, Agent, or Firm* — Wolf, Greenfield & Sacks, P.C.

(57) ABSTRACT

Methods, compositions of matter, and devices for delivering a therapeutic composition to a heart of a subject using a biopolymer scaffold material are described. In some embodiments, the biopolymer scaffold material including the therapeutic composition may be attached to a first cardiac tissue of a subject. The therapeutic composition is delivered from the biopolymer scaffold material to the heart of the subject.

18 Claims, 9 Drawing Sheets

(51) Int. Cl.
    *A61L 27/36*   (2006.01)
    *A61L 27/54*   (2006.01)

(56) References Cited

U.S. PATENT DOCUMENTS

| | | | |
|---|---|---|---|
| 9,308,225 | B2 | 4/2016 | Matheny |
| 2005/0013802 | A1* | 1/2005 | Dai .................... A61L 27/3604 |
| | | | 424/93.1 |
| 2005/0124560 | A1 | 6/2005 | Sung et al. |
| 2005/0181016 | A1 | 8/2005 | Freyman et al. |
| 2007/0014773 | A1 | 1/2007 | Matheny et al. |
| 2011/0293666 | A1* | 12/2011 | Wang ................... C12N 5/0698 |
| | | | 435/325 |
| 2012/0156255 | A1 | 6/2012 | Singh et al. |
| 2018/0071432 | A1 | 3/2018 | Christman et al. |
| 2018/0250441 | A1* | 9/2018 | Cornwell ................ A61L 27/50 |

OTHER PUBLICATIONS

Magden et al, "Composite sponges from sheep decellularized small intestinal submucosa for treatment of diabetic wounds", Jour of Biomat Applications, 2021, vol. 36, issue 1, pp. 112-127. First published Oct. 6, 2020. (Year: 2020).*
PCT/US2022/041425, Feb. 7, 2023, International Search Report and Written Opinion.
International Search Report and Written Opinion mailed Feb. 7, 2023 in connection with International Application No. PCT/US2022/041425.

* cited by examiner

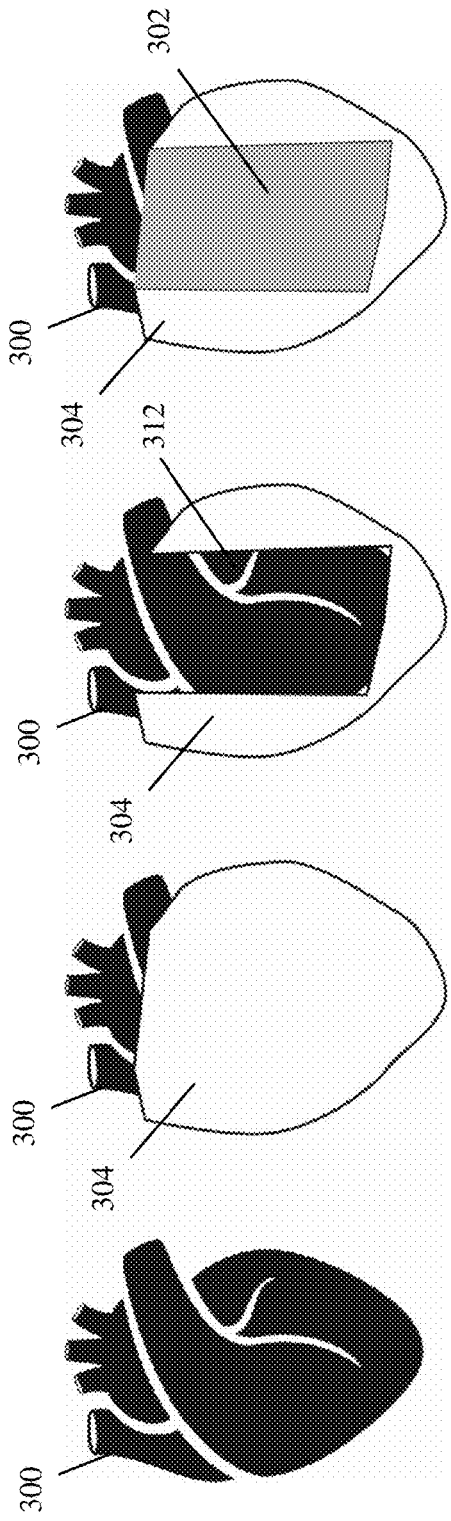
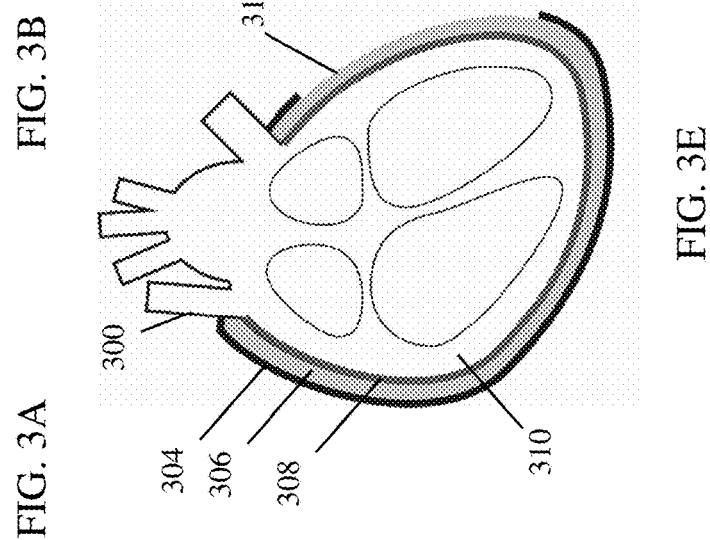
FIG. 3A  FIG. 3B  FIG. 3C  FIG. 3D
FIG. 3E  FIG. 3F

THERAPEUTIC COMPOSITION DELIVERY DEVICE

RELATED APPLICATIONS

This application claims the benefit of priority under 35 U.S.C. § 119(e) of U.S. Provisional Application Ser. No. 63/236,836, filed Aug. 25, 2021, the disclosure of which is incorporated herein by reference in its entirety.

BACKGROUND

Animal-derived, bioremodelable, biopolymer scaffold materials may be used to repair animal tissue including, for example, mammalian and more specifically human tissue. The term "bioremodelable" or "bioremodelability" refers to a material that lends itself to the breakdown by cells that occupy it and use it as a template for creating a replacement made up mainly of newly synthesized components secreted by the cells. Such materials are used in various heart tissue repair procedures.

SUMMARY

In some embodiments, a method of delivering a therapeutic composition to a heart of a subject comprises attaching a biopolymer scaffold material to a first cardiac tissue of the subject, wherein the biopolymer scaffold material comprises a decellularized extracellular matrix and a therapeutic composition. The method further comprises delivering the therapeutic composition from the biopolymer scaffold material to the heart of the subject. In some embodiments, the decellularized extracellular matrix may optionally be decellularized bovine or porcine extracellular matrix.

In some embodiments, a therapeutic composition delivery device comprises a biopolymer scaffold material configured to repair cardiac tissue, wherein the biopolymer scaffold material comprises a decellularized extracellular matrix that includes a plurality of interconnected pores. The therapeutic composition delivery device further comprises a therapeutic composition disposed in the pores of the biopolymer scaffold material. In some embodiments, the therapeutic composition may be configured to prevent or treat post-operative atrial fibrillation. In some embodiments, the decellularized extracellular matrix may optionally be decellularized bovine or porcine extracellular matrix.

In some embodiments, a kit to prevent or treat post-operative atrial fibrillation comprises a biopolymer scaffold material configured to repair cardiac tissue, wherein the biopolymer scaffold material comprises a decellularized extracellular matrix that includes a plurality of interconnected pores. The kit further comprises a therapeutic composition configured to prevent or treat post-operative atrial fibrillation. In some embodiments, the decellularized extracellular matrix may optionally be decellularized bovine or porcine extracellular matrix.

In some embodiments, a therapeutic composition delivery device comprises a biopolymer scaffold material configured to repair cardiac tissue, wherein the biopolymer scaffold material includes a plurality of interconnected pores, wherein the biopolymer scaffold material has a thickness equal to or greater than approximately 0.2 mm and less than or equal to approximately 6 mm, a porosity equal to or greater than approximately 20% and less than or equal to approximately 70%, and a tensile strength equal to or greater than approximately 5 MPa and less than or equal to approximately 60 MPa. The therapeutic composition delivery device further comprises a therapeutic composition disposed in the pores of the biopolymer scaffold material, wherein the therapeutic composition is configured to prevent or treat post-operative atrial fibrillation. In some embodiments the biopolymer scaffold material comprises decellularized extracellular matrix, wherein the decellularized extracellular matrix is decellularized bovine or porcine extracellular matrix.

It should be appreciated that the foregoing concepts, and additional concepts discussed below, may be arranged in any suitable combination, as the present disclosure is not limited in this respect. Further, other advantages and novel features of the present disclosure will become apparent from the following detailed description of various non-limiting embodiments when considered in conjunction with the accompanying figures.

In cases where the present specification and a document incorporated by reference include conflicting and/or inconsistent disclosure, the present specification shall control. If two or more documents incorporated by reference include conflicting and/or inconsistent disclosure with respect to each other, then the document having the later effective date shall control.

BRIEF DESCRIPTION OF DRAWINGS

The accompanying drawings are not intended to be drawn to scale. In the drawings, each identical or nearly identical component that is illustrated in various figures may be represented by a like numeral. For purposes of clarity, not every component may be labeled in every drawing. In the drawings:

FIGS. 3A-3F depict an embodiment of a procedure where a defect in heart tissue is repaired using a patch formed from a biopolymer scaffold material;

DETAILED DESCRIPTION

Figure 1A:
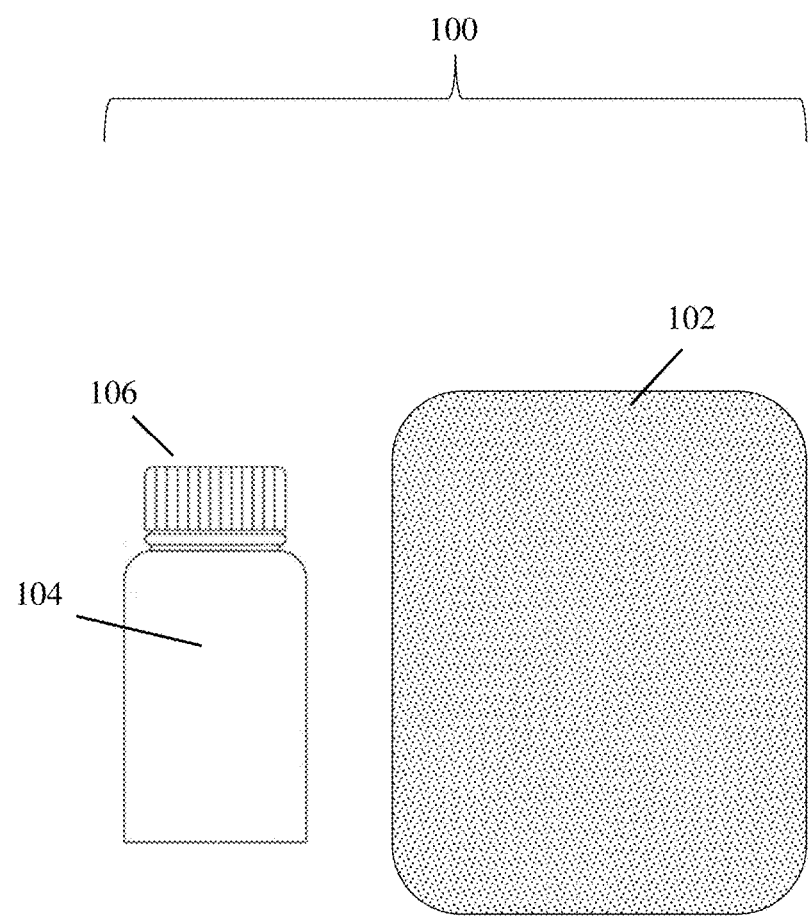
FIG. 1A is a schematic of a kit including a biopolymer scaffold material and a therapeutic composition, according to an embodiment.

Open heart cardiovascular procedures, such as coronary artery bypass grafting (CABG), valve replacement, or ventricular assist devices (VAD) implant procedures, are associated with a high rate of postoperative complications. Of those complications, postoperative atrial fibrillation (POAF) is extremely common, occurring in 30-50% of patients depending on the procedure and patient comorbidities. First onset of POAF occurs in a non-linear fashion, with a peak likelihood of incidence 2 to 3 days after surgery, and then decreases with time. POAF is associated with an increased risk of stroke and a 10-year increased risk of cardiovascular and all-cause mortality. Treatment for POAF may also result in significant additional costs for the patient.

An example of a therapeutic composition prescribed for preventing or treating POAF is amiodarone, a Class III antiarrhythmic drug that blocks voltage-gated potassium channels leading to prolonged repolarization of the cardiac action potential. Given orally, amiodarone has a slow onset of action. To achieve therapeutic concentrations of amiodarone in the myocardium, high oral doses of the drug must be given daily to the patient over a prolonged period of time. Systemic delivery (e.g., intravenous or oral) is associated with severe side effects on the thyroid, liver, lungs, skin and eyes. Local delivery of amiodarone has been investigated using several methodologies, including direct drug infusions into the pericardial fluid via a pump, and applications directly to the epicardium of the heart via spray-on gels or thin films, or with epicardial patches. However, these procedures and methods have been unable to deliver large enough concentrations over sufficiently long durations to provide clinically relevant therapeutic benefits either due to their loading capacity being too low and/or their delivery kinetics not being well matched for the desired dosing durations.

In view of the above, the inventors have recognized the benefits associated with biopolymer scaffold materials that are capable of delivering relatively large dosages of a therapeutic composition over longer durations of time as compared to prior therapeutic devices and procedures. Accordingly, embodiments related to a biopolymer scaffold with an appropriate combination of material parameters for delivering a desired therapeutic composition to cardiac tissue are described herein. In some embodiments, the biopolymer scaffold may be a decellularized extracellular matrix. For example, in some embodiments, the biopolymer scaffold may be a bovine extracellular matrix (EBM) which may be loaded with a desired therapeutic composition for delivery to a target heart tissue as described herein. In other embodiments, the biopolymer scaffold may be a porcine extracellular matrix which may be loaded with the desired therapeutic composition. Bovine, porcine extracellular matrix, or other appropriate biopolymer scaffold from any other appropriate source may be decellularized in some embodiments to remove the allogenic and/or xenogeneic cellular antigens from the scaffold to reduce and/or prevent an immune response to the scaffold. In some embodiments, the biopolymer scaffold material may be made using fetal (i.e., prebirth) or neonatal bovine dermis that is less than 10 weeks of age post birth, 26 weeks of age post birth, and/or 52 weeks of age post birth. In some embodiments, the biopolymer scaffold material may be made using adult porcine dermis or neonatal porcine dermis that is less than 10 weeks of age post birth, 26 weeks of age post birth, and/or 52 weeks of age post birth to provide a desired material thickness. Without wishing to be bound by theory, selecting tissue from animals of different ages within the above ranges may permit the formation of different biopolymer scaffold materials with different thicknesses, porosity, mechanical strength, collagen fiber architecture, and/or other desirable parameters. Additionally, in some embodiments, the therapeutic composition used with the biopolymer scaffold material may be a therapeutic composition for treating and/or preventing post-operative atrial fibrillation such as amiodarone, though other potential therapeutics may also be used as elaborated on below.

For the sake of clarity, the majority of embodiments and experiments discussed herein refer to the use and properties of decellularized bovine extracellular matrix (EBM). However, the noted properties and results should be understood as also being applicable to decellularized porcine extracellular matrix materials and/or other appropriate materials prepared using the methods disclosed herein.

In the above embodiment, the biopolymer scaffold material may be attached to a desired type of cardiac tissue including, but not limited to, the myocardium, epicardium, endocardium, pericardium, and/or the vessels leading to or from the heart. The therapeutic composition contained within the biopolymer scaffold material may then either be delivered to the cardiac tissue the scaffold is attached to and/or it may deliver the therapeutic composition to a second cardiac tissue located either adjacent to and/or downstream from the first cardiac tissue the scaffold is attached to. For example, in one specific embodiment, a biopolymer scaffold material may be attached to the pericardium of a subject and the therapeutic composition may diffuse out of the scaffold into the space surrounding the heart within the pericardial sac such that it delivers a therapeutically relevant dose to the myocardium of the subject.

In view of the above, the inventors have recognized and appreciated designs for a therapeutic composition delivery device that repairs or reconstructs defects in pericardial and/or epicardial tissue while also locally delivering a therapeutic composition to myocardial tissue for the prevention of POAF. In some embodiments, the device uses a specially configured version of EBM with characteristics that combine the properties of a repair patch and a reservoir for a therapeutic composition. EBM may also act as a physical barrier to inflammatory mediastinal constituents. The therapeutic compositions may be applied in the operating room during heart surgery and/or may be applied during manufacturing of EBM or any time prior to surgery. Of course, while the devices are described below with respect to heart tissue repairs, and specifically pericardial and/or epicardial repairs, and treatment for POAF, it should be noted that the disclosure is not so limited, and the device may be used in different applications in the body to repair other soft tissues and organs with different therapeutic compositions.

The characteristics of the biopolymer scaffold materials described herein make it especially suited for delivering therapeutic compositions to the heart when concurrently used as a repair patch. However, it should be noted that the biopolymer scaffold material may be made of any material that provides the desired combination of properties described herein. That said the EBM described herein is an example of a biopolymer scaffold material that has a desired combination of thickness, porosity, pore size, tortuosity, collagen fiber architecture, mechanical strength, biochemistry, surface properties, and/or other appropriate material parameters that make it well-suited as a biopolymer scaffold material in the therapeutic composition delivery device described herein.

In some embodiments, a biopolymer scaffold material may be provided in the form of a patch. The patch may have a patch body with a planar shape that is substantially larger in the width and/or length dimensions as compared to a thickness of the patch body. The patch body may also be relatively flexible such that it may be draped over and/or otherwise conform to the shape of a structure it is attached to during a surgical procedure. Of course, configurations of a device other than in the form of a patch body for use in repairing a pericardium, myocardium, or other heart tissue are also contemplated including, for example, applications such as heart valves, blood vessels, tendons, ligaments, and bone. This may correspond to structures formed with the disclosed biopolymer scaffold materials including, but not limited to, tubes, strips (with or without slits), patches with or without additional manufactured porosity added (e.g., additional holes up to 0.5 mm in diameter, extending fully or partially through a body made of the disclosed materials), and/or any other appropriate construction as the disclosure is not limited in this fashion.

Generally, EBM is a bioremodelable, biopolymer scaffold material derived from fetal, neonatal or post-natal animal tissue. EBM is processed in a way that preserves its tissue strength without reducing its intrinsic biological properties or compromising the ability of cells that occupy the tissue to remodel it. EBM may be used as a tissue-building component with or without cells for creating human body replacements.

According to some embodiments, EBM is produced from animal tissue by a method comprising the following steps: (1) removing the tissue from its source; (2) removing undesired cells, proteins, lipids, nucleic acids, and carbohydrates via chemical methods such as sodium chloride, hydrogen peroxide, sodium hydroxide, water and other optional solvents or chemicals; optionally extracting growth and differentiation factors from the tissue; (3) inactivating infective agents of the tissue; (4) mechanically expressing undesirable components from the tissue; (5) washing the tissue for removal of chemical residues; (6) optionally drying via lyophilization, supercritical CO2, air-drying, or other method; and (7) optionally cross-linking the tissue after chemical and mechanical treatment; and (8) optionally terminally sterilizing. As noted above, in some embodiments, EBM is made using fetal or neonatal bovine dermis that is any appropriate age that is less than 52 weeks of age, though embodiments in which tissue from an older animal is used is also contemplated. Again the tissue used to form the desired biopolymer scaffold material may be bovine dermis, porcine dermis, or any other appropriate tissue and/or source as the disclosure is not so limited. These manufacturing processes are further described in U.S. Pat. No. 9,011,895 which is incorporated herein by reference in its entirety for all purposes.

In some applications, it may be desirable to provide a particular collagen fiber architecture that is close to the collagen fiber architecture of the cardiac tissue that a biopolymer scaffold material is applied to. Accordingly, in some embodiments, the biopolymer scaffold material may include the following ranges and types of collagens. In some embodiments, the collagen contained in the matrix may be a native, intact, and/or non-denatured collagen from the original base matrix material. A biopolymer scaffold material, such as EBM, may include type I collagen in a dry weight percentage relative to the overall weight of the scaffold material that is greater than or equal to 60 wt %, 70 wt %, 75 wt %, 80 wt %, 90 wt % and/or any other appropriate range. The weight percentage of the type I collagen may also be less than or equal to 96%, 95%, 90 wt %, 85 wt %, 80 wt %, and/or any other appropriate range. The biopolymer scaffold material may also include a large quantity of type III collagen in a dry weight percentage relative to the overall weight of the scaffold material that is greater than or equal to 4 wt %, 5 wt %, 10 wt %, 15 wt %, 20 wt %, and/or any other appropriate range. Correspondingly, the weight percentage of type III collagen may be less than or equal to 40 wt %, 30 wt %, 25 wt %, 20 wt %, 10 wt %, and/or another appropriate range. Combinations of the above are contemplated including, for example, type I collagen in a range between or equal to 60 wt % and 95 wt % and type III collagen in a range between or equal to 5 wt % and 40 wt %, or more preferably 60 wt % to 80 wt % type I collagen as well as 20 wt % to 40 wt % type III collagen, may correspond to material formed from fetal and neonatal dermis. Correspondingly, type I collagen in a range around about 95 wt % and type III collagen around about 5 wt % may correspond to adult dermis. This difference in collagen type content may lead to different material properties. Of course, the inclusion of other types of collagens as well as weight percentages different than those noted above are also contemplated as the disclosure is not limited in this fashion.

The biochemistry of EBM makes it an ideal candidate as a biopolymer scaffold material for tissue repair. EBM does not incite significant inflammation because the manufacturing process does not significantly damage the native collagen fibers physically or biochemically. EBM may also be substantially free of xenogeneic growth factors that incite inflammation. In applications where EBM is used to provide a therapeutic composition to the myocardial tissue, EBM may not damage, injure, or otherwise further exacerbate any trauma to the myocardial tissues because it may be placed on the epicardium and/or pericardium in some embodiments rather than placed directly on the heart. EBM may also be devoid of measurable quantities of xenogeneic growth factors or extracellular matrix proteins that may cause inflammation which other scaffold materials may retain.

Another benefit of EBM is that it can be made in various thickness configurations that may be difficult, or impossible to practically obtain using other scaffold materials. In some embodiments, the unique fetal and neonatal bovine source allows EBM to be provided in a wide range of thicknesses and area ranges. In contrast, typical porcine dermis (another acellular dermal matrix not processed with the above noted processing techniques) uses horizontal splitting (cutting) to get uniformly thick materials which limits the thickness of this matrix which also includes different pore, mechanical, and biochemical properties. In contrast, small intestinal submucosa (SIS) and urinary bladder matrix materials inherently exhibit low-porosity, low absorption capacity, and low absorption rate in addition to being thinner materials that need several layers to be laminated together to provide increased thicknesses which impacts the internal properties of the matrix, and are typically provided with thicknesses less than 1 mm.

Benefits associated with increased thicknesses of the scaffold materials disclosed herein may include, for example, increased reservoir volumes for containing a therapeutic composition for long-duration release. Thus, in some embodiments, EBM, or other appropriate scaffold material, may have a thickness that is greater than or equal to about 1 mm, 2 mm, 3 mm, 4 mm, 5 mm, and/or any other appropriate thickness. Additionally, the thickness of EBM or other biopolymer scaffold material may be less than or equal to 6 mm, 5 mm, 4 mm, 3 mm, and/or any other appropriate thickness. Combinations of these thicknesses are contemplated including, for example, a scaffold thickness that is between or equal to 1 mm and 6 mm. Of course, thicknesses both greater than and less than those noted above are also possible.

Other benefits of EBM is its absorption rate and absorption capacity. EBM may be lyophilized, resulting in a highly porous membrane that can rapidly absorb large quantities of therapeutic compositions, which in some embodiments may be suspended in a carrier, even when provided in thickness greater than 1 mm thick configuration. Furthermore, EBM may be lyophilized at the end of manufacture, which, in combination with the thickness range of the device, leads to a device with extremely high liquid absorption characteristics. Thus, in some embodiments, a biopolymer scaffold matrix, such as EBM, may have an areal absorption capacity that is greater than or equal to 0.1 ml/cm$^2$, 0.2 ml/cm$^2$, 0.3 ml/cm$^2$, 0.4 ml/cm$^2$, 0.5 ml/cm$^2$, and/or any other appropriate absorption capacity (herein areal absorption capacity means volume of fluid per square area of EBM, however effective absorption capacity means volume of fluid per volume of EBM) and, depending on the therapeutic composition, may be saturated in less than 10 minutes. The areal absorption capacity may also be less than or equal to 1.0 ml/cm$^2$, 0.9 ml/cm$^2$, 0.8 ml/cm$^2$, 0.7 ml/cm$^2$, 0.6 ml/cm$^2$, and/or any other appropriate absorption capacity. Combinations of these ranges are contemplated including, for example, an areal absorption capacity that is between or equal to 0.1 ml/cm$^2$ and 1.0 ml/cm$^2$.

Depending on the mass of a given therapeutic composition, and the concentration of the therapeutic composition within a liquid absorbed into the biopolymer scaffold material, the therapeutic composition may be present in a range of areal densities. For example, a therapeutic composition, such as amiodarone in some embodiments, may be disposed in the pores of a biopolymer scaffold material (e.g., EBM), may have an areal density greater than or equal to 5 mg/cm$^2$, 6 mg/cm$^2$, 7 mg/cm$^2$, 10 mg/cm$^2$, and/or any other appropriate density. The areal density of the therapeutic composition may also be less than or equal to 30 mg/cm$^2$, 20 mg/cm$^2$, 10 mg/cm$^2$, 9 mg/cm$^2$, 8 mg/cm$^2$, 7 mg/cm$^2$, 6 mg/cm$^2$, and/or any other appropriate areal density. Combinations of the foregoing are contemplated including, for example, an areal density of a therapeutic composition contained within a biopolymer scaffold material that is between or equal to 5 mg/cm$^2$ and 10 mg/cm$^2$. In one specific example, amiodarone dissolved in a liquid at a concentration of 50 mg/mL might result in 1-5 mg/cm$^2$ of amiodarone loaded in the scaffold material. Of course, it should be understood that other ranges both greater than and less than those noted above are also contemplated.

In order to provide a desired amount of therapeutic composition to a subject, a desired amount of a therapeutic composition may be absorbed into the biopolymer scaffold material for a given application. For example, in some embodiments, an amount of amiodarone absorbed into a biopolymer scaffold material may be greater than or equal to 100 mg, 200 mg, 300 mg, 400 mg, 500 mg, 1000 mg, 2000 mg, and/or any other appropriate amount. Amounts of amiodarone absorbed into the biopolymer scaffold material may also be less than or equal to 3000 mg, 2000 mg, 1000 mg, 500 mg, and/or any other appropriate amount. Combinations of the foregoing are contemplated including, for example, an amount of amiodarone that is absorbed into a biopolymer scaffold material that is between or equal to 100 mg and 3000 mg. Of course, other combinations of the foregoing as well as ranges both greater than and less than the ranges noted above are also contemplated as the disclosure is not so limited.

While a biopolymer scaffold material may be provided pre-soaked with a desired therapeutic composition in a carrier liquid in some embodiments, in other embodiments, a user may soak the biopolymer scaffold material with the desired therapeutic composition prior to implantation. Due to the highly porous absorbent nature of the materials disclosed herein, the biopolymer scaffold material may be configured to absorb a desired amount of a therapeutic composition corresponding to the loadings disclosed herein in a time period that is less than or equal to 10 minutes, 5 minutes, 3 minutes, 2 minutes, 1 minute, and/or any other appropriate time period.

In contrast to the above, other scaffold materials may be thin compared to EBM and therefore incapable of absorbing these relatively large amounts of a therapeutic composition. For example, SIS is approximately 0.2 mm to 0.4 mm in thickness such that SIS would need multiple bonded layers to reach similar thicknesses, and even then, such a construction is unlikely to provide similar benefits due to the bonding process and inherent properties of the SIS itself. For instance, other materials, such as non-dehydrated materials like porcine acellular dermal matrix (e.g., Strattice) and SIS are either provided wet or hydrated, are dense with relatively little porosity, and/or have other limitations such that they do not allow for the device to hold such high loadings of a therapeutic composition and/or to be quickly soaked like a sponge in the operating room.

Due to the large source material, EBM, or other biopolymer scaffold materials as described herein, may be provided with a range of areas and/or shapes for various applications including any of the applications described previously above. Depending on the specific application, appropriate sizes for the scaffold material may include areas that are greater than or equal to 1 cm$^2$, 20 cm$^2$, 50 cm$^2$, and 100 cm$^2$, 150 cm$^2$, 200 cm$^2$, and/or any other appropriate size. The size of the scaffold material may also include areas that are less than or equal to 200 cm$^2$, 150 cm$^2$, 100 cm$^2$, 50 cm$^2$, 20 cm$^2$, and/or any other appropriate size. Combinations of the foregoing are contemplated including, for example, scaffold materials with areas that are between or equal to 1 cm$^2$ and 200 cm$^2$. Specific exemplary patch sizes that may be used in some applications may include, but are not limited to, 5×6 cm, 6×12 cm, 7×15 cm, 8×16 cm, 10×15 cm, or 10×20 cm. Of course, while specific size ranges are provided above, it should be understood that any appropriate size biopolymer scaffold material may be used including areas both greater than and less than those noted above as the disclosure is not limited in this fashion.

In some embodiments, EBM using bovine sources also has superior mechanical properties as compared to other typical biopolymer scaffold materials such as porcine dermis and SIS. For example, it is a strong, yet elastic material. By selecting for age, without splitting, and by nature of the collagen fiber architecture unique to the bovine source, EBM is extremely strong yet remains soft and pliable with stiffness similar to other human soft tissues (unlike most synthetic polymers, metals, or ceramics) including pericardium and myocardium. Thus, EBM based devices are mechanically strong (stronger than other scaffold materials such as SIS) such that they provide stable pericardial reconstruction and support. Additionally, EBM based devices may be compliant and soft such that they do not significantly affect heart function or result in mechanical rubbing and/or abrading of the myocardium when contacting the heart during normal sinus rhythm. Of course, while EBM may be preferable in some applications, it is expected that a biopolymer scaffold material made using porcine dermis and the above noted processing techniques will also exhibit superior absorption, release, thickness, and strength as compared to typical SIS materials.

In view of the above, a biopolymer scaffold material as disclosed herein, including an EBM, may have an ultimate tensile strength that is greater than or equal to 5 MPa, 10 MPa, 20 MPa, 30 MPa, 40 MPa, and/or any other appropriate tensile strength. The ultimate tensile strength may also be less than or equal to 60 MPa, 50 MPa, 40 MPa, 30 MPa, and/or any other appropriate tensile strength. Combinations of foregoing are contemplated including, for example, an ultimate tensile strength of a biopolymer scaffold material may be between or equal to 5 MPa and 60 MPa. Of course, tensile strengths both greater than and less than those noted above are also contemplated as the disclosure is not so limited.

A biopolymer scaffold material, such as EBM, may also have an improved suture pullout as compared to other materials. For example, a suture retention strength of the biopolymer scaffold material may be greater than or equal to 10 N, 20 N, 50 N, 100 N, 200 N, 300 N, and/or any other appropriate suture retention strength. The suture retention strength of the biopolymer scaffold material may also be less than or equal to 500 N, 400 N, 300 N, 200 N, 100 N, and/or any other appropriate suture retention strength. Combinations of the foregoing are contemplated including, for example, a suture retention strength that is between or equal to 10 N and 500 N. Of course, suture retention strengths both greater than and less than those noted above are also contemplated as the disclosure is not limited in this fashion. The above-noted suture retention strengths may be measured using a suture having a thickness equivalent to USP suture size/diameter for the intended procedure (4-0-2) during a standard suture pull out test.

In some instances, and as noted above, it may be desirable for a biopolymer scaffold material, such as EBM, to exhibit a desired amount of elasticity for cardiac applications. Accordingly, in some embodiments, a Young's modulus, sometimes referred to as an elastic modulus, of the biopolymer scaffold material may be greater than or equal to 3 MPa, 10 MPa, 20 MPa, 30 MPa, 40 MPa, 50 MPa, 100 MPa, 200 MPa, and/or any other appropriate range. The Young's modulus may also be less than or equal to 400 MPa, 300 MPa, 200 MPa, 100 MPa, 50 MPa, 40 MPa, 30 MPa, and/or any other appropriate range. Combinations of the foregoing are contemplated including, for example, between or equal to 1 MPa and 400 MPa as well as between or equal to 20 MPa and 200 MPa. Of course, while specific ranges are provided, ranges both greater than and less than those noted above are also contemplated as the disclosure is not limited in this fashion.

Another benefit of EBM is the tortuous interconnected open pore structure of the material. Thus, a biopolymer scaffold material may include a plurality of interconnected open pores that connect a first surface of the biopolymer scaffold material to an interior portion of the biopolymer scaffold material, and in some embodiments, a second opposing surface of the biopolymer scaffold material. A flow path extending through the plurality of interconnected pores may follow a tortuous, i.e., non-linear, path such that a liquid may flow into and subsequently out of the scaffold material during loading and eluting phases of the material. In some examples, the interconnected tortuous porosity of EBM is provided by the crisscrossing collagen fiber architecture of EBM. This porosity and architecture allow fluid to be absorbed quickly in a surgical setting (e.g., minutes) while still acting as a barrier against inflammation inducing molecules and/or providing the desired therapeutic composition elution properties.

A biopolymer scaffold material, such as EBM, used in the embodiments disclosed herein may have a porosity that is greater than or equal to 30%, 40%, 50%, and/or other appropriate porosity. The porosity may also be less than or equal to 80%, 70%, 60%, 50%, and/or any other appropriate porosity. Combinations of foregoing are contemplated including, porosities that are between or equal to 30% and 80%. However, porosities both greater than and less than those noted above are also contemplated as the disclosure is not so limited. Additionally, without wishing to be bound by theory, the high porosity nature of the materials disclosed herein may affect the overall volume and areal capacities of the materials.

A biopolymer scaffold material, such as EBM, used in the embodiments disclosed herein may have an average pore size that is greater than or equal to 1 µm, 2 µm, 5 µm, 10 µm, 50 µm, 100 µm, 250 µm, and/or any other appropriate size. The average pore size may also be less than or equal to 500 µm, 250 µm, 100 µm, 50 µm, and/or any other appropriate size. Combinations of foregoing are contemplated including, for example, an average pore size of a biopolymer scaffold material that is between or equal to 1 µm and 500 µm. Of course, average pore sizes both greater than and less than those noted above are also contemplated. Without wishing to be bound by theory, the pore sizes and tortuosity of the materials disclosed herein may affect the absorption rates of a therapeutic composition into the biopolymer scaffold material. For example, materials with larger pore sizes and decreased tortuosity, may exhibit faster rates during both absorption and elution as compared to materials exhibiting smaller pore sizes and increased tortuosity.

Due to the collagen fibers swelling and shrinking depending on the exposure of the biopolymer scaffold materials to a given liquid, the above porosities and average pore sizes may be measured in the dry state prior to introduction of a carrier liquid and/or therapeutic composition to the biopolymer scaffold material. Additionally, the pore sizes and porosity may be measured using microscopic optical image analysis.

In some embodiments, it may be desirable to improve the wicking capabilities of a biopolymer scaffold material. Such a modification may improve the ability of the biopolymer scaffold material to absorb liquids, may alter the elution kinetics of a therapeutic compound from the scaffold material, and/or may help to reduce the creation of unfilled occluded portions of the material due to the inclusion of air pockets in the matrix. Accordingly, in some embodiments, it may be desirable to include hydrophilic modifications and/or surface coatings within the pores of the biopolymer scaffold material. In such an embodiment, the surface modification and/or coating on the surface of the pores of the biopolymer scaffold material may be more hydrophilic, i.e., exhibit a lower water contact angle, than the underlying biopolymer scaffold material itself. Appropriate types of hydrophilic modifications and/or coatings may include, but are not limited to: polyethylene glycol (PEG), crosslinked collagen; degradable polymers such as poly(lactic acid) (PLA), poly (glycolic acid) (PGA), and P4HB; and/or permanent polymers. Of course, embodiments in which a hydrophilic modification and/or coating are not used are also contemplated.

As described above, a biopolymer scaffold material, such as EBM, acts as a reservoir for a therapeutic composition. When the scaffold material containing a therapeutic composition is attached to tissue in a subject, the device may locally deliver the therapeutic composition from the scaffold material to adjacent tissues and/or other tissues located adjacent to and/or downstream from the scaffold material.

Another benefit of the disclosed biopolymer scaffold materials, including EBM, are the therapeutic composition release characteristics that allow for therapeutic composition delivery in a specified therapeutic window. The therapeutic compositions may not bind strongly to the collagen of the device. Also, the porosity and fluid flow characteristics of biopolymer scaffold material slow down the release of the therapeutic composition as compared to a bolus or simple injection delivery to the pericardial fluid. Due to these properties, in some embodiments, the release and/or accumulation of a therapeutic composition in a target volume and/or tissue may increase over the first several days, resulting in a peak therapeutic concentration in a target tissue within the heart at a time between 1 day and 5 days, 2 days and 4 days, and/or more preferably at about 3 days after implantation. Without wishing to be bound by theory, providing a desired therapeutic concentration of a therapeutic composition in a time range around 3 days may be desirable for applications such as treating and/or preventing postoperative atrial fibrillation which sees the largest rate of occurrence on or around day 3. In some embodiments, a minimum elution rate and/or concentration of the therapeutic composition may continue to be delivered from the device to the target heart tissue for 28 days, 20 days, 10 days, 7 days, and/or any other appropriate time period. Since this release of the therapeutic composition is local, it may reduce the systemic load of amiodarone, or other therapeutic composition, to other organs and tissues. Delivery may also occur fast enough that the several days of pre-loading used in other surgical procedures to reach a desired therapeutic concentration may be unnecessary.

It should be understood that the desired peak concentration may be different for different therapeutic compositions. However, in the case of amiodarone, a desired peak therapeutic concentration that is between or equal to 1 µg/g and 500 µg/g 1000 in the target tissue within the noted time periods above may be desired in some embodiments. The minimum therapeutic concentration may be maintained for the time periods noted above after the peak. The minimum therapeutic concentration may be less than a corresponding peak therapeutic concentration and in some embodiments may be between or equal to 1 µg/g and 20 µg/g in the target tissue. The expected concentrations of the therapeutic composition in a target tissue may be evaluated using an appropriate animal model as detailed in the examples below.

It should be understood that while the properties and characteristics for a biopolymer scaffold material provided above and elsewhere in the current disclosure are primarily described relative to EBM, these properties and characteristics may be found in other biopolymer scaffold materials as well. For example, decellularized porcine extracellular matrix materials and/or other appropriate materials prepared using the methods described herein may exhibit the properties and characteristics described herein.

In some embodiments, it may be desirable to provide directionality to the delivery of a therapeutic composition. For example, it may be desirable to reduce, or substantially prevent, the elution of a therapeutic composition from one surface of a scaffold material while permitting the therapeutic composition to elute from a second opposing surface of the scaffold material. In one such embodiment, it may be desirable to deliver a therapeutic composition to the heart while preventing delivery of the therapeutic composition to the sternal side of a patch made from the scaffold material. Appropriate barriers that may be applied to, or otherwise disposed on, a surface of the scaffold material may include, but are not limited to: polyethylene glycol (PEG), cross-linked collagen; degradable polymers such as poly(lactic acid) (PLA), poly(glycolic acid) (PGA), and P4HB; permanent polymers; and/or any other appropriate material capable of reducing the diffusion rate and/or completely blocking the passage of the therapeutic composition. In such an embodiment, at least a portion, and in some embodiments the entirety, of the opposing surface of the scaffold material may be substantially free of the barrier material such that the therapeutic composition may be eluted from the uncovered surface. Depending on the embodiment, the barrier may either be a separate layer disposed on a surface of the scaffold material and/or the barrier may be disposed in the pores adjacent to the surface of the scaffold material as the disclosure is not limited as to how the barrier layer is formed.

As used herein, the term "therapeutic composition" (also referred to interchangeably as a "drug" or "therapeutic agent") refers to a composition that is administered to a subject to treat a disease, disorder, or other clinically recognized condition, or for prophylactic purposes, and has a clinically significant effect on the body of the subject to treat, prevent, and/or diagnose the disease, disorder, or condition. The therapeutic composition may be delivered to a subject in a quantity greater than a trace amount to affect a therapeutic response in the subject. In some embodiments, therapeutic compositions can include, but are not limited to, any synthetic or naturally-occurring biologically active compound or composition of matter which, when administered to a subject (e.g., a human or nonhuman animal), induces a desired pharmacologic, immunogenic, and/or physiologic effect by local and/or systemic action. For example, useful or potentially useful within the context of certain embodiments are compounds or chemicals traditionally regarded as drugs, vaccines, and biopharmaceuticals. Certain such therapeutic compositions may include molecules such as proteins, peptides, hormones, nucleic acids, gene constructs, cells (e.g., autologous cells, allogeneic cells, and/or any other appropriate type of cell), etc., for use in therapeutic, diagnostic, and/or enhancement areas. In certain embodiments, the therapeutic composition is a small molecule and/or a large molecule. Accordingly, it should be understood that the therapeutic compositions described herein are not limited to any particular type of therapeutic composition.

In some embodiments, and as noted above, a therapeutic composition may be a therapeutic composition used to prevent and/or treat postoperative atrial fibrillation. Appropriate therapeutic compositions for this purpose, may include, but are not limited to, antiarrhythmic therapeutic compositions such as amiodarone; lidocaine; magnesium; and/or any other appropriate therapeutic composition capable of preventing and/or treating postoperative atrial fibrillation.

To facilitate absorption of a desired therapeutic composition into a biopolymer scaffold matrix, in some embodiments, a therapeutic composition may be dissolved, dispersed, and/or otherwise mixed with a carrier liquid. Appropriate types of carrier liquids may include, but are not limited to: water; saline; polysorbate; alcohol including benzyl alcohol, methanol, ethanol, or other appropriate type of alcohol; plasma; serum; other bodily fluids, and/or any other appropriate type of carrier. Of course, embodiments in which a carrier liquid is not used are also contemplated.

It should be understood that the biopolymer scaffold materials disclosed herein may be used for any appropriate applications within the heart, and/or other portions of the body. Appropriate applications may include, but are not limited to, pericardium repair, epicardial support and repair, myocardial repair, mitral valve replacement, other cardiac applications, and/or any other appropriate application as the disclosure is not limited in this fashion.

Turning to the figures, specific non-limiting embodiments are described in further detail. It should be understood that the various systems, components, features, and methods described relative to these embodiments may be used either individually and/or in any desired combination as the disclosure is not limited to only the specific embodiments described herein.

As shown in FIG. 1A, the devices and therapeutic compositions described herein can be provided as a kit 100 for repairing or reconstructing soft tissue defects while serving as a local therapeutic composition delivery method directly to the repaired soft tissues. The kit 100 can include one or more biopolymer scaffold materials 102 for repairing soft tissues. The scaffold materials may come in many different shapes and sizes or may be cut to size during a repair procedure, depending on need. A quantity of one or more therapeutic compositions 104 may also be provided. Such compositions may be provided in a liquid form, e.g., as a pure liquid, suspension, solution or emulsion, or as a crystalline or powdered solid, or even in gaseous form. Such substance(s) can be provided in a dispensing bottle or container 106. The therapeutic composition can be provided in such containers in pre-measured volumes or doses.

In some embodiments, a surgeon or medical professional may open a kit 100 and remove the scaffold material 102 and the container 106 holding the therapeutic composition 104. The therapeutic composition 104 may be applied to the scaffold material in the operating room prior to a soft tissue repair procedure. For example, the scaffold material 102 may be soaked in the therapeutic composition 104 when the therapeutic composition is supplied in liquid form. However, embodiments in which the therapeutic composition is already preloaded into the scaffold material and is ready for use by a surgeon or other medical professional are also contemplated.

In some embodiments, the therapeutic composition 104 may include a therapeutic composition for preventing or treating POAF after heart surgery. For example, the therapeutic composition may include amiodarone. In some embodiments, the therapeutic composition may include amiodarone combined with other small molecules such as lidocaine, magnesium, beta-blockers, statins, and/or any other appropriate therapeutic composition. These components may have synergistic effects when used in combination by affecting both potassium and calcium channels in the myocardium, helping to prevent the risk of POAF. Of course, other types of therapeutic compositions intended to treat postoperative atrial fibrillation and/or therapeutic compositions for treating other types of conditions may be used with the materials and devices disclosed herein as the disclosure is not so limited.

In some embodiments, a therapeutic composition may be applied to a biopolymer scaffold material in the operating room and/or preloaded onto the scaffold 102 during manufacturing or prior to being assembled in a kit 100. In an epicardial repair, for example, a therapeutic composition 104 of amiodarone optionally combined with one or more of magnesium, lidocaine, beta-blockers, and/or statins may be supplied in a container, such as vial 106, of kit 100, and the scaffold material 102 may be soaked in the therapeutic composition 104 in the operating room prior to the repair procedure. In some embodiments, amiodarone, magnesium, lidocaine, and/or any other appropriate therapeutic composition may be pre-loaded onto the scaffold material 102. For example, magnesium may be preloaded onto the scaffold 102 and/or amiodarone may be preloaded into the scaffold via various methods, such as precipitation and/or crystallization. In scaffold materials 102 pre-loaded with amiodarone, additional amiodarone may be added in liquid formulation in the operating room, provided as part of the therapeutic composition 104. The combination of precipitated and liquid amiodarone can increase the concentration of amiodarone delivered to the heart and also make the delivery bimodal with faster release via liquid and slower release via the crystallized amiodarone. Embodiments in which this two-phase delivery concept is used for other therapeutic compositions are also contemplated in which a first therapeutic composition may be provided in a liquid form that is applied just prior to implantation and a solid form of either the same therapeutic composition and/or a second different therapeutic composition may be preloaded within the pores of the scaffold material. Similar to the above, the first therapeutic composition loaded in the liquid form may undergo a first elution rate and the solid therapeutic composition may undergo a second slower elution rate.

Figure 1B:
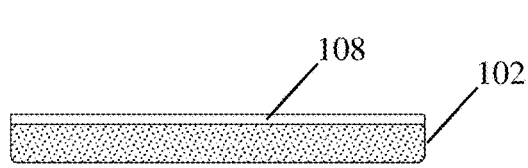
FIG. 1B is a schematic of a biopolymer scaffold material including a barrier layer, according to an embodiment.
Figure 1C:
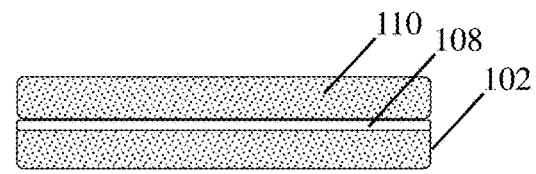
FIG. 1C is a schematic of a device including a two biopolymer scaffold material layers with a barrier layer disposed between the scaffold material layers, according to an embodiment.

As noted above, in some embodiments, it may be desirable to provide directionality for a therapeutic composition eluted from a device as disclosed herein. One such embodiment is shown in FIG. 1B in which a barrier layer 108 is disposed on, or in, a first surface of the scaffold 102 such that the therapeutic composition may be eluted from an opposing second surface of the scaffold. Correspondingly, the barrier may reduce, and in some embodiments, substantially prevent, the elution of the therapeutic composition from the surface of the scaffold the barrier layer is positioned on. In yet another embodiment, it may be desirable to provide different therapeutic compositions to different structures adjacent to opposing surfaces of a scaffold material, see FIG. 1C. In such an embodiment, the first scaffold material 102 and barrier layer 108 disposed thereon may be used to apply a first therapeutic composition to a first structure, such as the heart. A second scaffold material 110 may be disposed on a surface of the barrier layer opposite from the first scaffold material. The second scaffold material may be loaded with a second therapeutic composition such that the second composition is eluted from the exterior surface of the second scaffold material but is substantially prevented from diffusing through the barrier layer. For example, lidocaine or another pain reliever might be included in the second scaffold material. In such an embodiment, a first therapeutic composition may be delivered to the heart from a heart oriented surface of the device while the other therapeutic composition, such as the disclosed pain reliever, may be delivered to the sternum from a sternal oriented surface of the device. Thus, the disclosed devices may be used to deliver different therapeutic compositions to different anatomical structures located on opposite sides of a device.

Figure 2B:
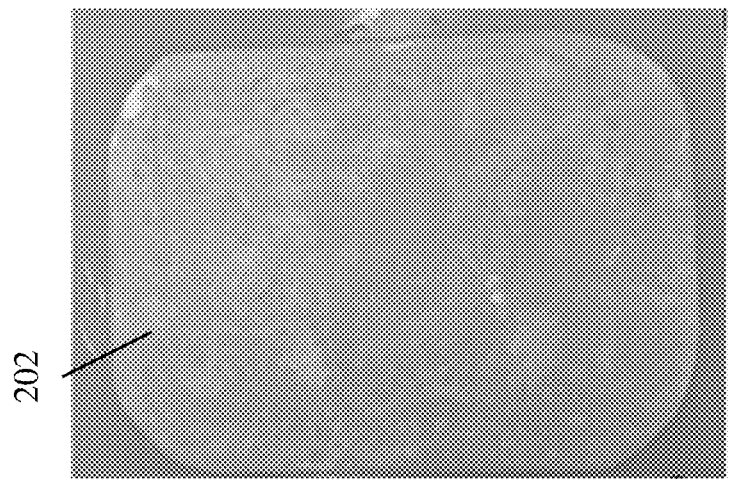
FIG. 2B is an image of the biopolymer scaffold material of FIG. 2A after the soaking step with the biopolymer scaffold material saturated with the therapeutic composition.
Figure 2A:
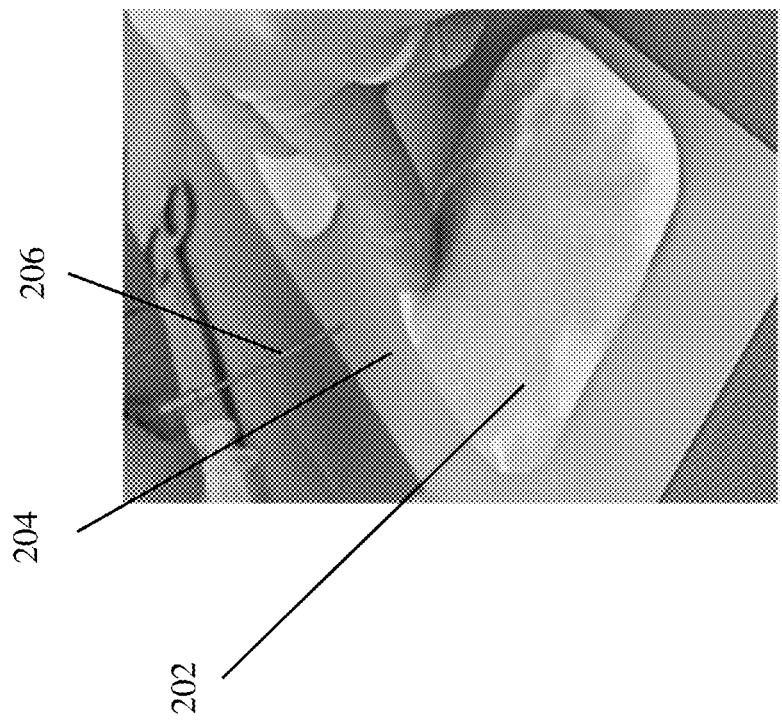
FIG. 2A is an image of a biopolymer scaffold material during a soaking step in a therapeutic composition, according to an embodiment.

FIG. 2A shows an embodiment of a biopolymer scaffold 202 during a soaking process in a therapeutic composition 204 and FIG. 2B shows a biopolymer scaffold 202 fully soaked in the therapeutic composition 204. As shown in FIG. 2A, a medical professional uses a syringe 206 or other applicator to apply the therapeutic composition 204 to the scaffold material 202. A sufficient amount of therapeutic composition 204 may be applied to the scaffold 202 until the scaffold is fully saturated, as shown in FIG. 2B. Embodiments in which the scaffold material is simply immersed in a solution are also contemplated as the disclosure is not limited to how the scaffold material is exposed to the therapeutic composition. After a sufficient duration to permit the desired amount of therapeutic composition to be absorbed into the scaffold material, the scaffold material may then be used for a desired repair or other surgical procedure.

As shown in FIGS. 3A-3F, a device 302, in the form of a patch, including a biopolymer scaffold material and a therapeutic composition may be used to repair or reconstruct a defect 312 in a heart 300 of a patient. Depending on the specific embodiment, the defect may either be pre-existing on the heart and/or the defect may be a result of heart surgery. As best shown in the cross-sections of FIGS. 3E and 3F, in some embodiments, a heart 300 may include a defect 312 in the pericardium 304. The tissue may be repaired by the device 302 that is either overlain on and attached to the pericardium at locations located outwards from the defect or the device may be attached to the edges of the defect as the disclosure is not so limited. Depending on the particular application, the device may be attached to the tissue either using sutures, a surgical adhesive, and/or any other appropriate attachment method. After being attached, the therapeutic composition may flow from the device 302 into the myocardium 310 of the heart 300. Of course, while repair of a defect in the pericardium is depicted, it should be understood that the disclosed devices may also be used to repair defects in other tissues including the epicardium 308 which is spaced from the pericardium by the pericardial sac 306, the myocardium 310, as well as any other appropriate heart tissue as the disclosure is not so limited. Regardless of the specific location, in some embodiments, the device may be loaded with a therapeutic composition including, for example, a therapeutic composition for treating and/or preventing postoperative atrial fibrillation. In some embodiments, the therapeutic composition may include amiodarone, magnesium, beta-blockers, statins, lidocaine, combinations of the above, and/or any other appropriate therapeutic compositions which have been shown not to adversely impact the biochemical or mechanical properties of the biopolymer scaffold material.

The device may simultaneously serve multiple functions. The device may stabilize the heart like the native pericardium. The device may also act as a physical separation barrier between the heart and chest of the patient to reduce or prevent inflammatory mediastinal blood products, considered instigators of postoperative atrial fibrillation, from reaching the heart. Further, due to its biochemistry, the device 302 may result in reduced, or no inflammation as compared to other comparable repair patches. The device 302 may also minimize injury to the myocardium by not requiring direct therapeutic composition application to the myocardium (e.g., via glue, suture, etc.). Incorporating the device into native heart tissue further prevents long-term complications from the device itself. The device may also provide a reservoir for delivering a therapeutic composition locally to the heart, while confining the therapeutic composition within the pericardial space. The device may deliver therapeutic concentrations of the therapeutic composition in the desired time frame as noted above. Thus, negative side effects in the patient caused by high doses of amiodarone may be minimized or eliminated.

Figure 4:
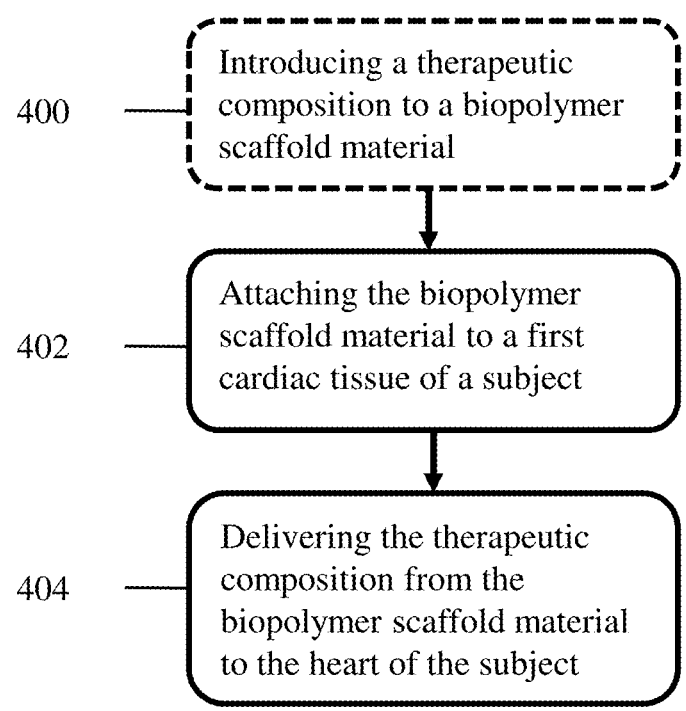
FIG. 4 is a method for delivering a therapeutic composition to heart tissue, according to an embodiment.

A method of delivering a therapeutic composition to a heart is shown in FIG. 4. In step 400, a therapeutic composition is introduced to a biopolymer scaffold material. Step 400 may be carried out in an operating room during a procedure intended to repair a heart tissue defect with the scaffold material. In some embodiments, as discussed above, the scaffold material may be in the form of a patch soaked in the therapeutic composition right before the scaffold material is attached to the heart tissue of a subject. Alternatively, step 400 may be performed during manufacturing of the scaffold material or at some time prior to the surgical procedure, such that the scaffold material is preloaded with therapeutic agents at the time of the procedure. A scaffold pre-loaded with a therapeutic composition may or may not be soaked in additional therapeutic agents at the time of surgery. Thus, step 400 is an optional step in the described method, as denoted by the dashed lines enclosing step 400.

In step 402, the biopolymer scaffold material is attached to a first cardiac tissue of a subject. The scaffold material may be used to repair or reconstruct a tear or defect in the heart of the subject. The scaffold material may be attached to epicardial and/or pericardial tissue of the heart. In step 404, the therapeutic composition in the scaffold material is delivered from the scaffold material to the heart of the subject. The scaffold material may act as a reservoir for the therapeutic composition. Once the scaffold is attached to the heart tissue, the therapeutic composition may be delivered from the scaffold material to myocardial tissue of the heart through the epicardial and/or pericardial tissue. Thus, local delivery of the therapeutic composition directly to the myocardial tissue is achieved without directly contacting the myocardium.

It should be noted that although the biopolymer scaffold material has been described as a device for repairing heart tissue and locally delivering a therapeutic composition to the heart, the scaffold material may be used in other applications, as the disclosure is not so limited.

Example: Animal Model Testing

The safety of soaking EBM, in an intravenous formulation of amiodarone was tested in a large animal model of pericardial repair. Specifically, EBM under the tradename CardiaMend™ was used. The device was approximately 1 mm thick (range 0.75-1.54 mm). An ovine model was used for a pericardial repair procedure. Briefly, a piece of EBM measuring 7 cm by 10 cm was soaked to saturation in 6 mL of 50 mg/mL amiodarone hydrochloride. The EBM patch was then inserted through a hole cut through the pericardium via a mini-thoracotomy approach and secured with sutures at the margins of the pericardial defect. Following closure of the superficial muscle and skin, the animals were recovered, and housed until sacrifice at 3 days, 7 days, and 28 days. A total of 7 sheep were used, which included duplicates at each time point and a control animal which received IV amiodarone of 1000 mg/day via IV for 14 days. Following sacrifice, the repair site was explored, and the implant and heart were grossly evaluated for signs of inflammation, scarring, or fibrosis. Gross images were acquired. Tissue was then harvested from relevant areas and preserved for amiodarone quantification by LC/MS analysis following tissue homogenization and methanol extraction.

Figure 5A:
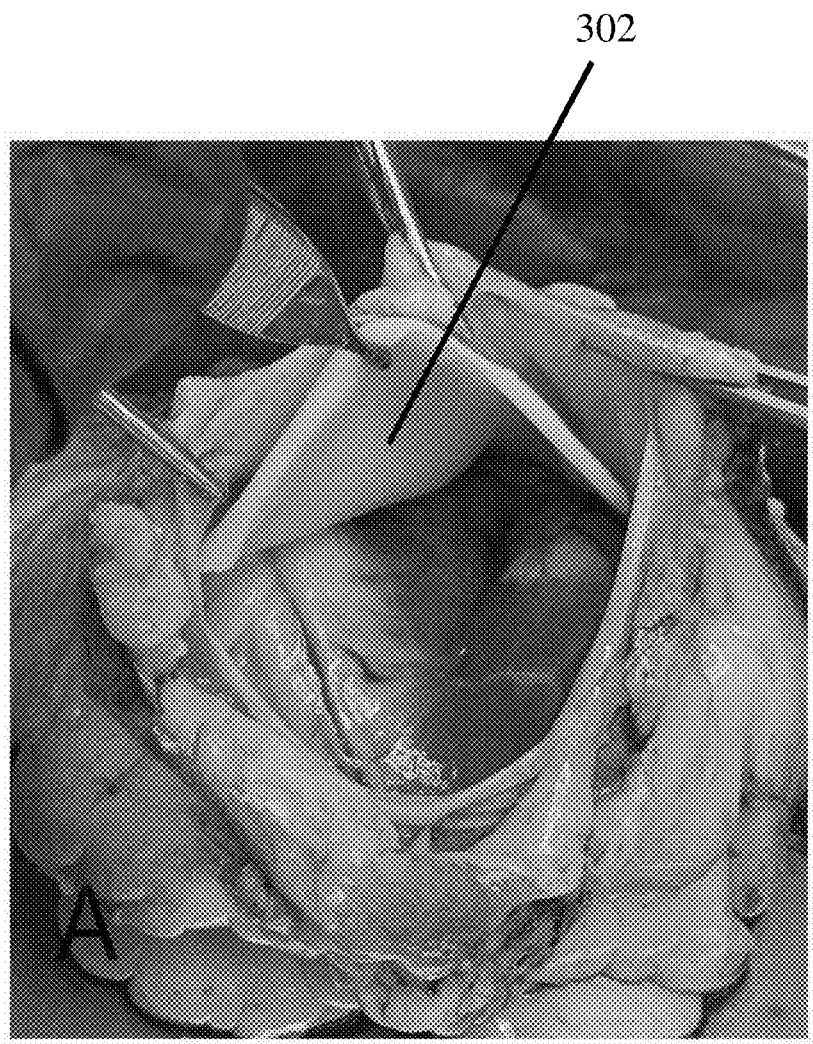
FIG. 5A is an image of a bovine extracellular biological matrix (EBM) patch at 3 days of use as a pericardial repair patch in sheep.
Figure 5B:
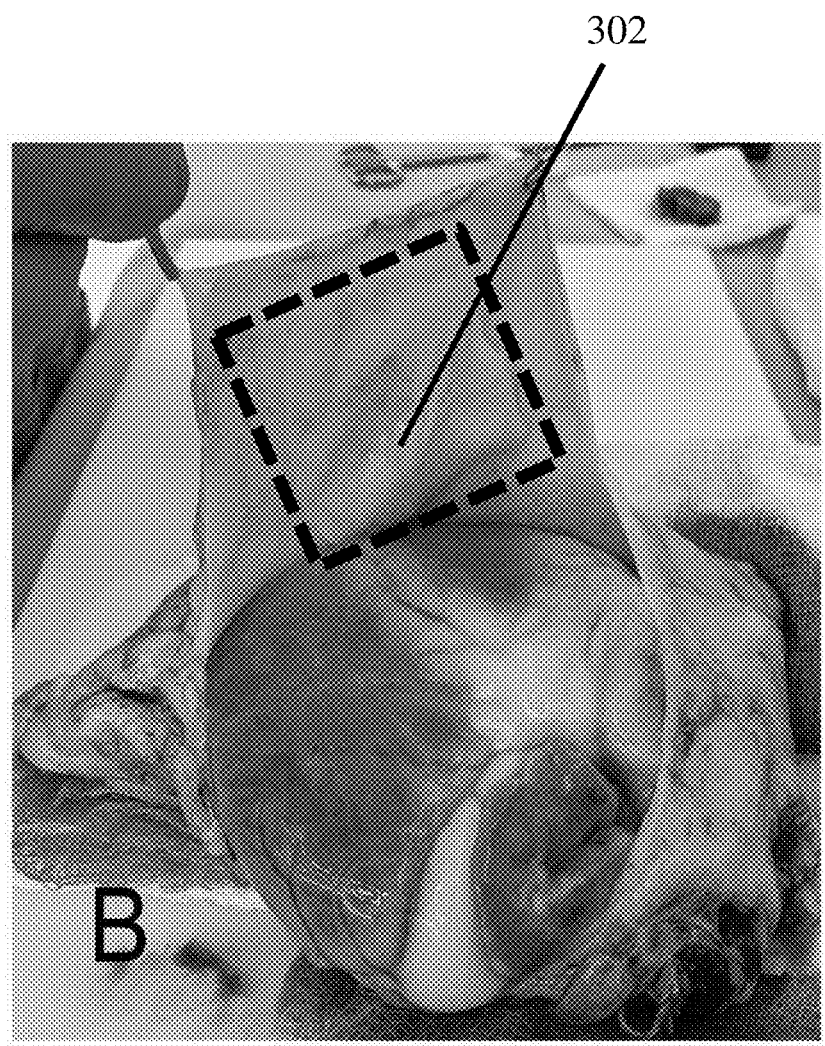
FIG. 5B is an image of an EBM patch at 28 days of use as a pericardial repair patch in sheep.

The results demonstrated that soaking EBM in amiodarone caused no safety concerns and had no effect on the efficacy of EBM as a pericardial repair device. All animals survived to the scheduled date of sacrifice and had no abnormal clinical signs as reported by the study veterinarian. FIGS. 5A-5B show the results of the implemented EBM patch 302 used within this trial. The evaluated results using this device are shown at 3 and 28 days by FIG. 5A and FIG. 5B, respectively. Under gross evaluation at both 3 days and 28 days, the EBM patch 302 was intact, there were no attachments or adhesions to the epicardium, and the heart had no signs of inflammation or fibrosis.

Average tissue concentrations of amiodarone in the myocardium of 64 µg/g (range 7.3 µg/g to 158 µg/g) were found in the sheep at 3 days with very little found in the liver or blood plasma (Table 1). The myocardial concentrations of amiodarone at day 3 were consistent with therapeutically active concentrations that have been found in clinical studies. By 28 days, the average concentration of amiodarone in the myocardium dropped to 7.8 µg/g (range Not Detected to 102 µg/g) and was below the limit of detection in the liver and blood plasma. These values at 3 days were greater than those in the control animal after 14 days of IV amiodarone loading.

TABLE 1

Quantification of Amiodarone Concentration in Relevant Tissues at the Target Times of Days 3 and 28

|  | Day 3 Average (µg/g) | Day 28 Average (µg/g) |
| --- | --- | --- |
| Myocardium | 63.50 | 7.82 |
| Liver | 2.61 | 0.02 |
| Blood Plasma | 2.55 | 0.00 |

Average tissue concentrations of amiodarone from day 3-7 were also evaluated. Specifically, amiodarone concentration in the left and right atria were 96 µg/g and 83 µg/g respectively with very little of the drug found in the liver or lungs (Table 2). Concentrations in the ventricles (14 µg/g) were lower than those observed in the atria. These atrial concentrations of amiodarone from day 3 to day 7 are consistent with therapeutically active concentrations that have been found in clinical studies. Additionally, the concentrations of amiodarone in the organs prone to amiodarone toxicity (liver and lung) were lower with a local single dose of amiodarone compared to a maximum chronic IV therapy.

TABLE 2

Quantification of Amiodarone Concentration in Relevant Tissues at the Target Time of Days 3-7 Compared to the Control Tissues with the Maximum Amiodarone Loading (1,000 mg/day via IV for 14 Days)

|  | EBM drug delivery Day 3-7 Average (µg/g) | Maximum IV delivery - positive control Average (µg/g) |
| --- | --- | --- |
| Left Atrium | 96 | 19 |
| Right Atrium | 83 | 33 |
| Ventricles | 14 | 9 |
| Liver | 1 | 8 |
| Lung | 4 | 27 |

Example: Capacity Comparisons

Figure 6:
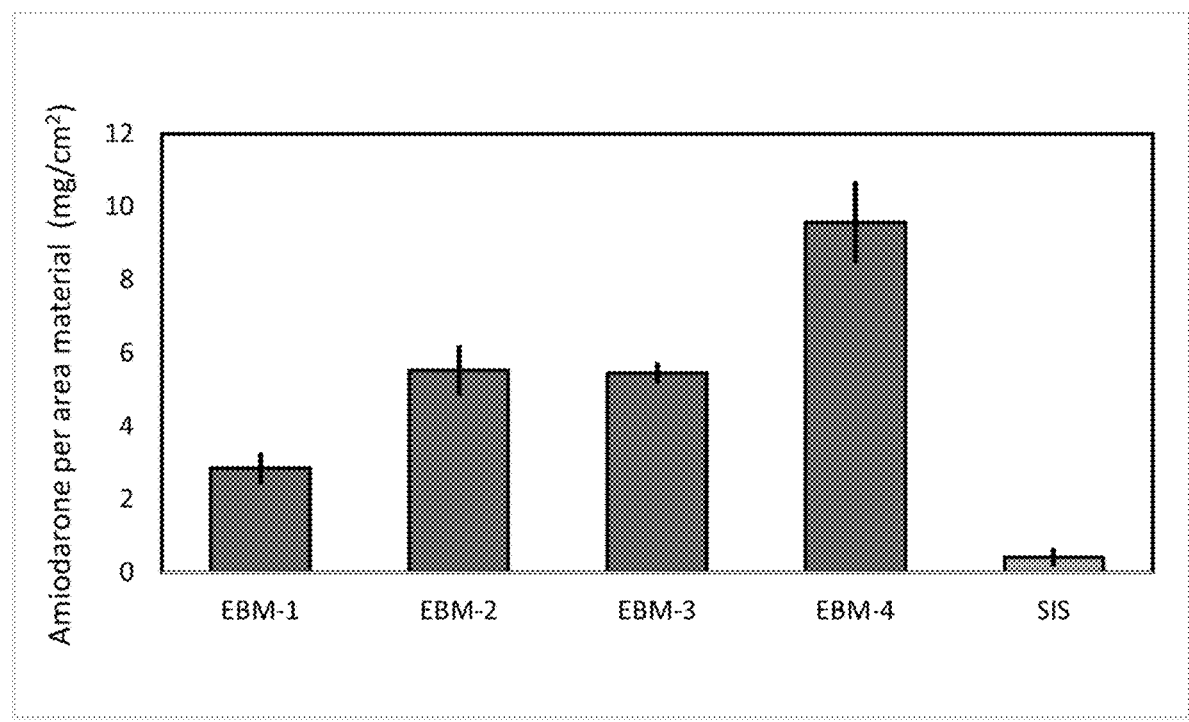
FIG. 6 is a graph comparing absorption capacity of amiodarone in EBM of varying thickness and in porcine small intestinal submucosa (SIS), in vitro.
Figure 7:
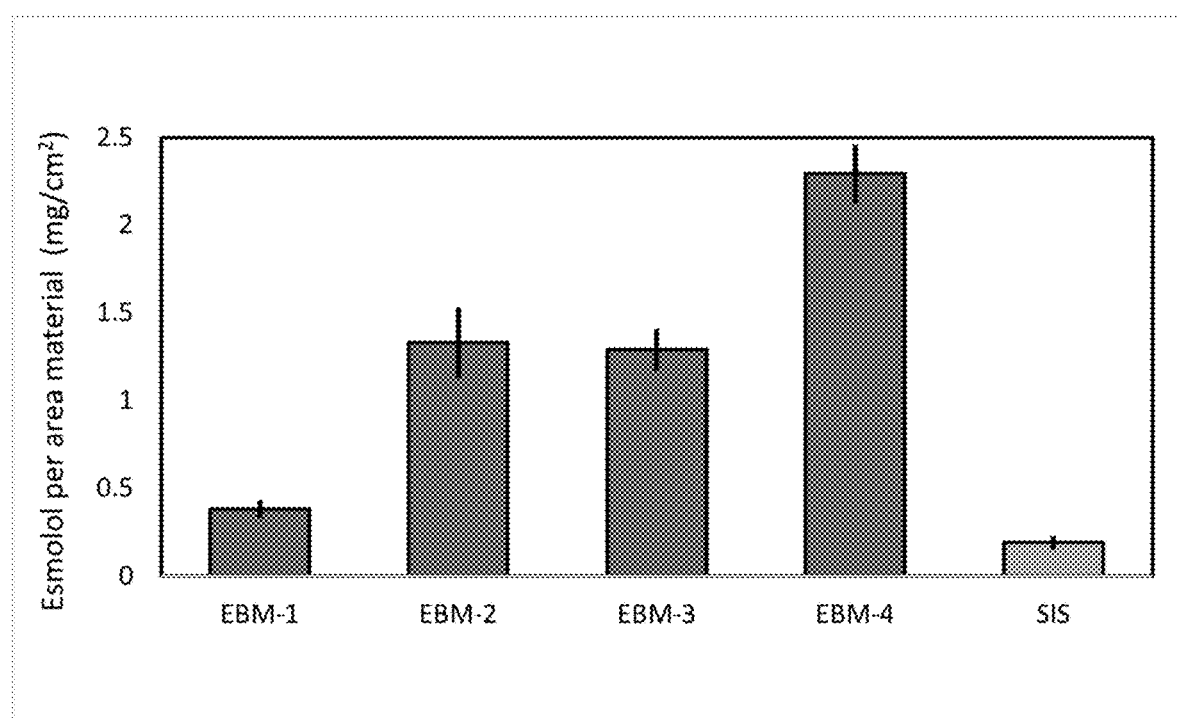
FIG. 7 is a graph comparing absorption capacity of esmolol in EBM of varying thickness and in SIS, in vitro.
Figure 8:
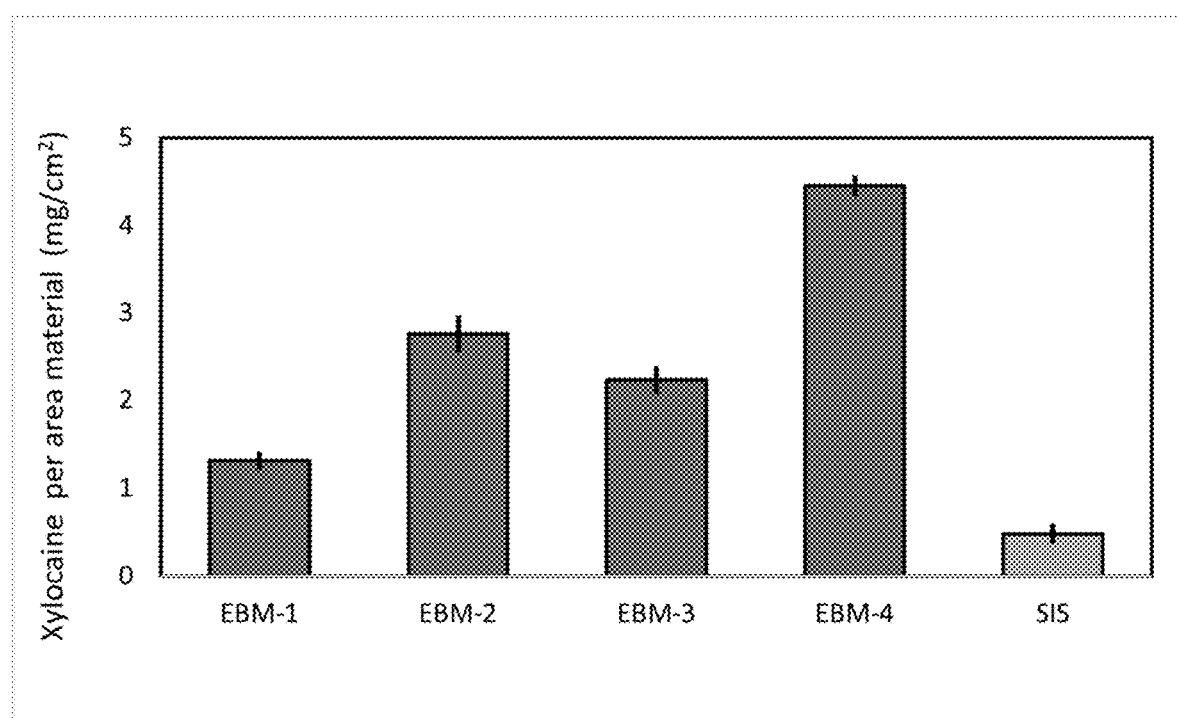
FIG. 8 is a graph comparing absorption capacity of xylocaine in EBM of varying thickness and in SIS, in vitro.

Absorption capacities of three different drug types were experimentally determined for EBM patches of varying thicknesses and SIS. The results of these experiments are shown in FIG. 6, FIG. 7, and FIG. 8, respectively. The drug types tested were an antiarrhythmic medication (amiodarone), a beta-blocker (esmolol), and a pain reliever (xylocaine). To specify the naming conventions for FIGS. 6-8, EBM-1, EBM-2, EBM-3, and EBM-4 refer to EBMs with material thickness ranges of 0.25-0.66 mm, 0.90-1.28 mm, 1.12-1.38 mm, and 2.00-2.62 mm, respectively. Similarly, for FIGS. 6-8, SIS refers to the previously mentioned biopolymer scaffold material small intestinal submucosa, which is a typically used scaffolding material. The thickness range of SIS tested for FIGS. 6-8 was 0.14-0.25 mm.

The testing procedure for the above absorption capacity experiments was as follows. Material dimensions and mass measurements were collected for the dry weight of the EBM and SIS matrix prior to the addition of the drug types. The dry material was then soaked to saturation directly with one of the drug types (amiodarone, esmolol, or xylocaine). The drug was allowed to saturate into the matrix material without any additional additives. The soaked weight of the material was then recorded and by using both the soaked and dry weight of the material, the mass of absorbed drug was calculated. Similarly, using the material dimensions collected, the areas of the matrix material were calculated. Using both the mass of the drug and these dimensional parameters, the average active drug ingredient per unit area, also known as the absorption capacity of the material, was then calculated in units of $mg/cm^2$. This process was repeated for each of the thickness ranges of EBM and SIS materials for each of the amiodarone, esmolol, and xylocaine drug trials. Standard deviation values for the average absorption capacities of each of the trials were calculated and are depicted with the error bars on the graphs shown in FIGS. 6-8.

The results shown in FIGS. 6-8 demonstrated that across all the drug types and material thicknesses tested, the EBM performed significantly better than the SIS material in the metric of average ingredient per unit area, even in view of standard deviation in the average measurements. For example, the EBM-4 material in the amiodarone trial shown in FIG. 6 had an average ingredient per area of 9.57 $mg/cm^2$ compared to an average ingredient per area of 0.41 $mg/cm^2$ for the SIS matrix material. Moreover, the smallest thickness range EBM material for the amiodarone trial, EBM-1, had an average ingredient per area of 2.84 $mg/cm^2$ which is still much greater than that of the SIS material with a similar thickness. Not only was the EBM material able to obtain high absorption capacity of the drug types as shown in FIGS. 6-8, but EBM is able to provide this high absorption capacity without degradation to the EBM matrix, see for example, the animal model testing above where the EBM patch was able to maintain functionality and deliver sustained release of the drug to the tissue area over a period of at least 28 days. Hence, the characteristics of the EBM matrix material are advantageous as compared to typical scaffold materials such as SIS as they provide high drug absorption capacities and sustained delivery of drugs without any adverse effects observed in the EBM over the observed durations.

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

The invention claimed is:

1. A therapeutic composition delivery device comprising:
a biopolymer scaffold material configured to be attached to cardiac tissue, wherein the biopolymer scaffold material comprises a decellularized extracellular matrix that includes a plurality of interconnected pores; and
a therapeutic composition disposed in the pores of the biopolymer scaffold material,
wherein the biopolymer scaffold material is a repair patch, wherein the decellularized extracellular matrix is a decellularized bovine extracellular matrix and comprises fetal or neonatal tissue, wherein the therapeutic composition comprises greater than or equal to 200 mg of amiodarone, and wherein the biopolymer scaffold material has an areal absorption capacity of liquid of equal to or greater than approximately 0.1 ml/cm² and less than or equal to approximately 1ml/cm².

2. The therapeutic composition delivery device of claim 1, wherein the therapeutic composition is configured to prevent and/or treat post-operative atrial fibrillation.

3. The therapeutic composition delivery device of claim 1, wherein the cardiac tissue comprises pericardial, epicardial, and/or myocardial tissue.

4. The therapeutic composition delivery device of claim 1, wherein the therapeutic composition further comprises at least one selected from lidocaine, magnesium, beta-blockers, and statins.

5. The therapeutic composition delivery device of claim 1, wherein the biopolymer scaffold material comprises 200 mg to 3000 mg of amiodarone.

6. The therapeutic composition delivery device of claim 1, wherein the biopolymer scaffold material has a thickness of equal to or greater than approximately 0.2 mm and less than or equal to approximately 6 mm.

7. The therapeutic composition delivery device of claim 1, wherein the biopolymer scaffold material has a surface area of equal to or greater than approximately 1 cm² and less than or equal to approximately 200 cm².

8. The therapeutic composition delivery device of claim 1, wherein the biopolymer scaffold material has a porosity of equal to or greater than approximately 20% and less than or equal to approximately 70%.

9. The therapeutic composition delivery device of claim 1, wherein the biopolymer scaffold material has a tensile strength of equal to or greater than approximately 3 MPa and less than or equal to approximately 60 MPa.

10. The therapeutic composition delivery device of claim 1, wherein the biopolymer scaffold material has a suture retention strength of equal to or greater than approximately 10 N and less than or equal to approximately 500 N.

11. A therapeutic composition delivery device comprising:
a biopolymer scaffold material configured to repair cardiac tissue, wherein the biopolymer scaffold material includes a plurality of interconnected pores, wherein the biopolymer scaffold material has a thickness of equal to or greater than approximately 0.2mm and less than or equal to approximately 6 mm, a porosity of equal to or greater than approximately 20% and less than or equal to approximately 70%, and a tensile strength of equal to or greater than approximately 3 MPa and less than or equal to approximately 60MPa; and
a therapeutic composition disposed in the pores of the biopolymer scaffold material,
wherein the biopolymer scaffold material is a repair patch, wherein the decellularized extracellular matrix is a decellularized bovine extracellular matrix and comprises fetal or neonatal tissue, wherein the therapeutic composition comprises greater than or equal to 200mg of amiodarone, and wherein the biopolymer scaffold material has an areal absorption capacity of liquid of equal to or greater than approximately 0.1 ml/cm² and less than or equal to approximately 1 ml/cm².

12. The therapeutic composition delivery device of claim 11, wherein the therapeutic composition is configured to prevent or treat post-operative atrial fibrillation.

13. The therapeutic composition delivery device of claim 12, wherein the therapeutic composition further comprises at least one of lidocaine, magnesium, beta-blockers, and statins.

14. The therapeutic composition delivery device of claim 11, wherein the cardiac tissue comprises pericardial, epicardial, and/or myocardial tissue.

15. The therapeutic composition delivery device of claim 11, wherein the biopolymer scaffold material has a surface area of equal to or greater than approximately 1 cm² and less than or equal to approximately 200 cm².

16. The therapeutic composition delivery device of claim 11, wherein the biopolymer scaffold material has a suture retention strength of equal to or greater than approximately 10 N and less than or equal to approximately 500 N.

17. The therapeutic composition delivery device of claim 14, wherein the delivery device is configured to deliver the therapeutic composition to the cardiac tissue over a time period of greater than or equal to 2 days and less than or equal to 28 days.

18. The therapeutic composition delivery device of claim 11, wherein the delivery device is configured to deliver the therapeutic composition to the cardiac tissue over a time period of greater than or equal to 2 days and less than or equal to 28 days.

* * * * *

UNITED STATES PATENT AND TRADEMARK OFFICE
CERTIFICATE OF CORRECTION

PATENT NO. : 12,194,017 B2
APPLICATION NO. : 17/895004
DATED : January 14, 2025
INVENTOR(S) : Kevin Cornwell et al.

Page 1 of 1

It is certified that error appears in the above-identified patent and that said Letters Patent is hereby corrected as shown below:

In the Claims

At Column 20, Lines 47 and 48, "claim 14" should read -- claim 1 --

Signed and Sealed this
Eleventh Day of February, 2025

Coke Morgan Stewart
*Acting Director of the United States Patent and Trademark Office*